(12) United States Patent
Fang et al.

(10) Patent No.: US 11,400,175 B2
(45) Date of Patent: Aug. 2, 2022

(54) APPARATUS AND METHOD TO MEASURE CONCENTRATION OF DISINFECTANT IN MEDICAL DEVICE REPROCESSING SYSTEM

(71) Applicant: ASP Global Manufacturing GmbH, Schaffhausen (CH)

(72) Inventors: Yan Fang, Irvine, CA (US); Nick N. Nguyen, Silverado, CA (US); Kaitao Lu, Irvine, CA (US)

(73) Assignee: ASP Global Manufacturing GmbH, Schaffhausen (CH)

( * ) Notice: Subject to any disclaimer, the term of this patent is extended or adjusted under 35 U.S.C. 154(b) by 346 days.

(21) Appl. No.: 16/792,475

(22) Filed: Feb. 17, 2020

(65) Prior Publication Data

US 2020/0179545 A1   Jun. 11, 2020

Related U.S. Application Data

(62) Division of application No. 15/157,952, filed on May 18, 2016, now Pat. No. 10,702,619.

(51) Int. Cl.
*A61L 2/18* (2006.01)
*A61B 1/12* (2006.01)
(Continued)

(52) U.S. Cl.
CPC ............ *A61L 2/18* (2013.01); *A61B 1/00057* (2013.01); *A61B 1/123* (2013.01); *A61B 1/125* (2013.01); *A61B 90/70* (2016.02); *A61L 2/24* (2013.01); *G01N 21/80* (2013.01); *G01N 31/22* (2013.01); *A61B 2090/701* (2016.02);
(Continued)

(58) Field of Classification Search
CPC .................................. A61B 90/70; A61L 2/18
See application file for complete search history.

(56) References Cited

U.S. PATENT DOCUMENTS 5,438,002 A   8/1995 Mallard de la Varende et al.
5,932,987 A   8/1999 McLoughlin
(Continued)

FOREIGN PATENT DOCUMENTS

BR   200505186 A   4/2008

OTHER PUBLICATIONS

Chinese Office Action and Search Report dated Dec. 29, 2020 for Application No. 201710347420.0, 7 pages.
(Continued)

*Primary Examiner* — Donald R Spamer
(74) *Attorney, Agent, or Firm* — Frost Brown Todd LLC (57) ABSTRACT

A medical instrument processor includes an enclosure, a liquid distribution system, and a disinfectant concentration measuring subsystem. The enclosure is configured to hold a medical instrument. The liquid distribution system is configured to deliver a disinfection solution to a medical instrument within the enclosure. The liquid distribution system has a liquid outlet. The disinfectant concentration measuring subsystem includes a first mixing chamber in fluid communication with the liquid outlet, a pump that is configured to simultaneously pump the disinfection solution and the reagent solution into the first mixing chamber, and a concentration analysis assembly that is operable to determine a concentration of disinfectant in a sample solution that is output from the first mixing chamber. The reservoir is in fluid communication with the first mixing chamber.

20 Claims, 6 Drawing Sheets

FUNCTIONAL DIAGRAM — OPTICAL (51) Int. Cl.
   *A61B 1/00* (2006.01)
   *A61L 2/24* (2006.01)
   *G01N 21/80* (2006.01)
   *A61B 90/70* (2016.01)
   *G01N 31/22* (2006.01)

(52) U.S. Cl.
   CPC ........ *A61L 2202/11* (2013.01); *A61L 2202/14* (2013.01); *A61L 2202/15* (2013.01); *A61L 2202/17* (2013.01); *A61L 2202/24* (2013.01)

(56) References Cited

U.S. PATENT DOCUMENTS

| | | |
|---|---|---|
| 6,585,934 B1 | 7/2003 | Oberleitner et al. |
| 6,986,736 B2 | 1/2006 | Williams et al. |
| 7,479,257 B2 | 1/2009 | Nguyen et al. |
| 7,686,761 B2 | 3/2010 | Jackson et al. |
| 8,246,909 B2 | 8/2012 | Williams et al. |
| 8,472,024 B2 | 6/2013 | Preiner et al. |
| 10,201,269 B2 | 2/2019 | Yang et al. |
| 10,702,619 B2 | 7/2020 | Fang et al. |
| 2008/0309930 A1 | 12/2008 | Rensen |
| 2013/0045380 A1 | 2/2013 | Lewis et al. |

OTHER PUBLICATIONS

Experimental Biosciences, David Caprette, Rice University, last modified Aug. 10, 2012, 9 pgs.

English machine translation of Ibrahim et al., BR 200505186, Apr. 15, 2008, 13 pgs.

European Search Report, Extended, and Written Opinion dated Jan. 17, 2018 for Application No. EP 17171501.4, 12 pgs.

APPARATUS AND METHOD TO MEASURE CONCENTRATION OF DISINFECTANT IN MEDICAL DEVICE REPROCESSING SYSTEM

This application is a continuation of U.S. patent application Ser. No. 15/157,952, entitled "Apparatus and Method to Measure Concentration of Disinfectant in Medical Device Reprocessing System," filed on May 18, 2016, issued as U.S. Pat. No. 10,702,619 on Jul. 7, 2020.

BACKGROUND

The below discussion relates to the reprocessing (i.e., decontamination) of endoscopes and other instruments that are used in medical procedures. In particular, the below discussion relates to an apparatus and a method that may be used to reprocess a medical device such as an endoscope after the medical device has been used in a first medical procedure, such that the medical device may be safely used in a subsequent medical procedure. While the below discussion will speak mainly in terms of an endoscope, it should be understood that the discussion may also equally apply to certain other medical devices.

An endoscope may have one or more working channels or lumens extending along at least a portion of the length of the endoscope. Such channels may be configured to provide a pathway for passage of other medical devices, etc., into an anatomical region within a patient. These channels may be difficult to clean and/or disinfect using certain primitive cleaning and/or disinfecting techniques. Thus, the endoscope may be placed in a reprocessing system that is particularly configured to clean endoscopes, including the channels within endoscopes. Such an endoscope reprocessing system may wash and disinfect the endoscope. Such an endoscope reprocessing system may include a basin that is configured to receive the endoscope, with a pump that flows cleaning fluids over the exterior of the endoscope within the basin. The system may also include ports that couple with the working channels of the endoscope and associated pumps that flow cleaning fluids through the working channels of the endoscope. The process executed by such a dedicated endoscope reprocessing system may include a detergent washing cycle, followed by a rinsing cycle, followed by a sterilization or disinfection cycle, followed by another rinsing cycle. The sterilization or disinfection cycle may employ disinfection solution and water rinses. The process may optionally include an alcohol flush to aid displacement of water. A rinsing cycle may be followed by an air flush for drying and storage.

Examples of systems and methods that may be used to reprocess a used endoscope are described in U.S. Pat. No. 6,986,736, entitled "Automated Endoscope Reprocessor Connection with Integrity Testing," issued Jan. 17, 2006, the disclosure of which is incorporated by reference herein; U.S. Pat. No. 7,479,257, entitled "Automated Endoscope Reprocessor Solution Testing," issued Jan. 20, 2009, the disclosure of which is incorporated by reference herein; U.S. Pat. No. 7,686,761, entitled "Method of Detecting Proper Connection of an Endoscope to an Endoscope Reprocessor," issued Mar. 30, 2010, the disclosure of which is incorporated by reference herein; and U.S. Pat. No. 8,246,909, entitled "Automated Endoscope Reprocessor Germicide Concentration Monitoring System and Method," issued Aug. 21, 2012, the disclosure of which is incorporated by reference herein. An example of a commercially available endoscope reprocessing system is the EVOTECH® Endoscope Cleaner and Reprocessor (ECR) by Advanced Sterilization Products of Irvine, Calif.

In order for the sterilization or disinfection cycle of an endoscope reprocessing system to be effective, it may be important to ensure that the disinfection solution is sufficiently concentrated. In systems where the disinfection solution is re-circulated and re-used within an endoscope reprocessing system to clean multiple endoscopes, the disinfectant in the disinfection solution may become increasingly diluted, particularly by any residual rinse water that remains in the system after the rinsing cycles occur. Consequently, it may be prudent to assess the disinfectant concentration in the disinfection solution between cycles, and replace the disinfection solution when it becomes too diluted to be effective.

Some conventional systems and techniques may provide manual methods for assessing the disinfectant concentration in the disinfection solution of an endoscope reprocessing system. For example, the system user may expose a test strip to a sample of the disinfection solution and observe the strip for a color change that is indicative of a disinfectant concentration that is below an effective concentration. Because such a test strip method is subjective, it may be inaccurate. Moreover, the test strip method may increase the risk of operator exposure to the disinfectant. Alternatively, the system operator may send a sample of the disinfection solution to a third party laboratory to measure the disinfectant concentration via high performance liquid chromatography. In addition to being time consuming and costly, this method may also increase the risk of operator exposure to the disinfectant.

The concentration of certain disinfectants, such as aldehydes, can be measured by passing a light through a sample containing the disinfectant, and measuring its absorbance via an automated process that is integrated with an endoscope reprocessing system. However, this method may be characterized by a number of limitations. For example, the aldehyde concentration in the sample may need to be relatively low, otherwise the aldehyde might absorb all of the light passed through the sample, which may make a meaningful absorbance reading impossible. Moreover, the accuracy of this method may be vulnerable to potential interference materials in the solution, such as bio-burden and/or aging/oxidation by-products in the sample. It may therefore be desirable to provide a system and method that is not sensitive to potential interference materials in the disinfectant solution; and that is usable within a broad range of disinfectant concentration.

While a variety of systems and methods have been made and used to reprocess medical devices, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Medical Device Reprocessing Apparatus

Figure 1:
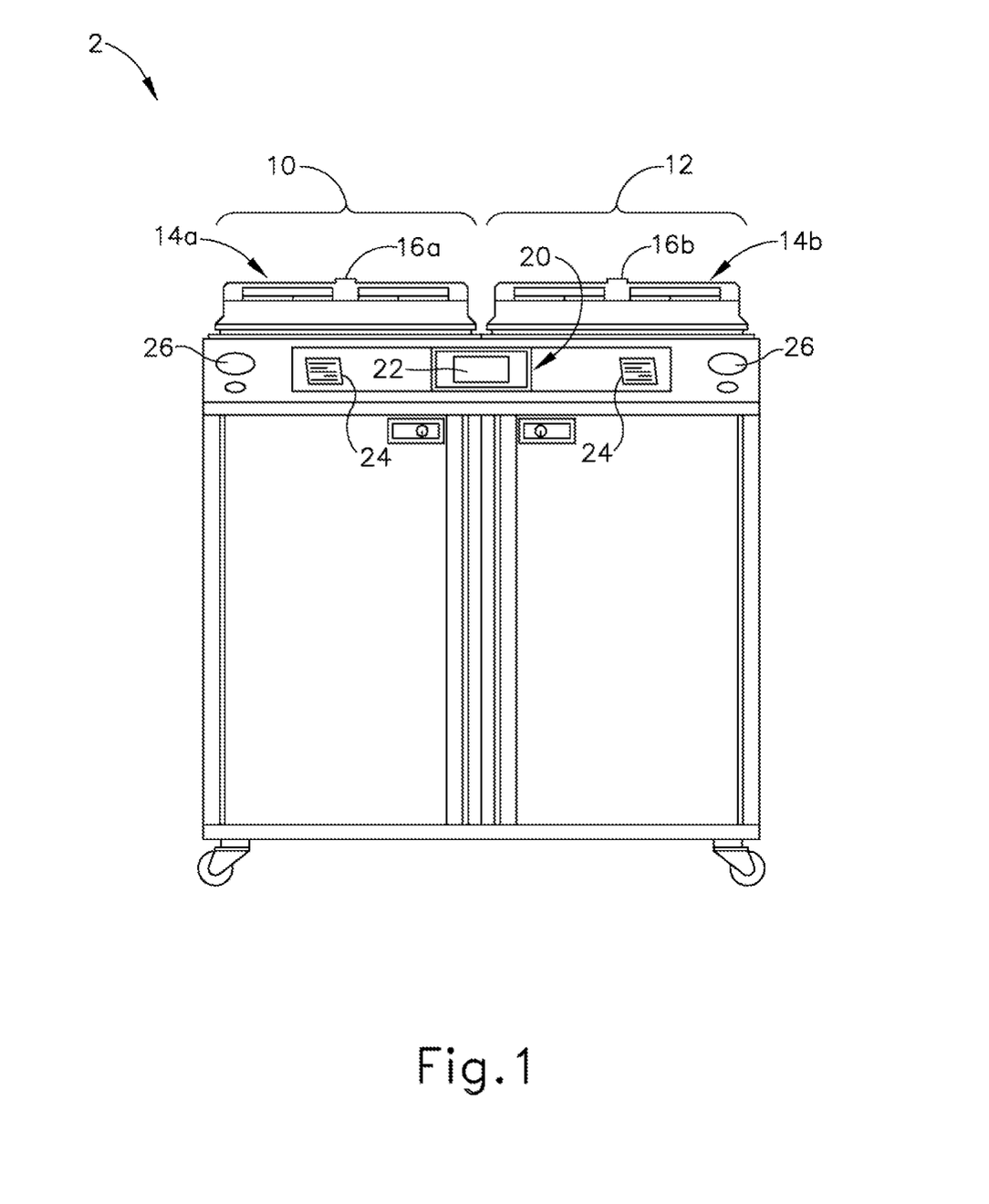
FIG. 1 depicts a front elevational view of an exemplary reprocessing system.
Figure 2:
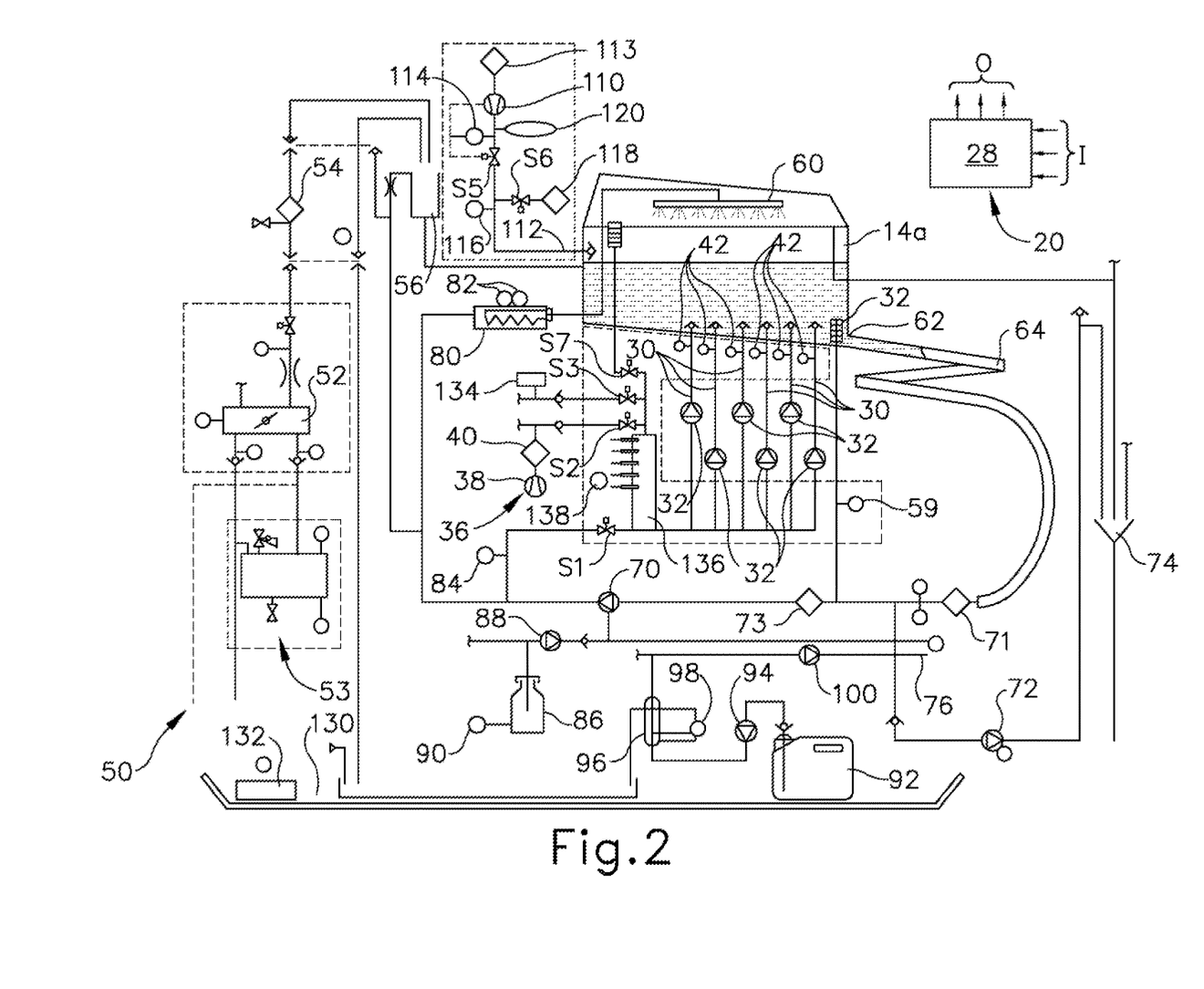
FIG. 2 depicts a schematic diagram of the reprocessing system of FIG. 1, with only a single decontamination basin shown for clarity.

FIGS. 1-2 show an exemplary reprocessing system (2) that may be used to decontaminate endoscopes and other medical devices that include channels or lumens formed therethrough. System (2) of this example generally includes a first station (10) and a second station (12). Stations (10, 12) are at least substantially similar in all respects to provide for the decontamination of two different medical devices simultaneously or in series. First and second decontamination basins (14a, 14b) receive the contaminated devices. Each basin (14a, 14b) is selectively sealed by a respective lid (16a, 16b). In the present example, lids (16a, 16b) cooperate with respective basins (14a, 14b) to provide a microbe-blocking relationship to prevent the entrance of environmental microbes into basins (14a, 14b) during decontamination operations. By way of example only, lids (16a, 16b) may include a microbe removal or HEPA air filter formed therein for venting.

A control system (20) includes one or more microcontrollers, such as a programmable logic controller (PLC), for controlling decontamination and user interface operations. Although one control system (20) is shown herein as controlling both decontamination stations (10, 12), those skilled in the art will recognize that each station (10, 12) can include a dedicated control system. A visual display (22) displays decontamination parameters and machine conditions for an operator, and at least one printer (24) prints a hard copy output of the decontamination parameters for a record to be filed or attached to the decontaminated device or its storage packaging. It should be understood that printer (24) is merely optional. In some versions, visual display (22) is combined with a touch screen input device. In addition or in the alternative, a keypad and/or other user input feature is provided for input of decontamination process parameters and for machine control. Other visual gauges (26) such as pressure meters and the like provide digital or analog output of decontamination or medical device leak testing data.

FIG. 2 diagrammatically illustrates just one decontamination station (10) of reprocessing system (2), but those skilled in the art will recognize that decontamination station (12) may be configured and operable just like decontamination station (10). It should also be understood that reprocessing system (2) may be provided with just one single decontamination station (10, 12) or more than two decontamination stations (10, 12).

Decontamination basin (14a) receives an endoscope (200) (see FIG. 3) or other medical device therein for decontamination. Any internal channels of endoscope (200) are connected with flush conduits, such as flush lines (30). Each flush line (30) is connected to an outlet of a corresponding pump (32), such that each flush line (30) has a dedicated pump (32) in this example. Pumps (32) of the present example comprise peristaltic pumps that pump fluid, such as liquid and air, through the flush lines (30) and any internal channels of endoscope (200). Alternatively, any other suitable kind of pump(s) may be used. In the present example, pumps (32) can either draw liquid from basin (14a) through a filtered drain (34) and a valve (S1); or draw decontaminated air from an air supply system (36) through a valve (S2). Air supply system (36) of the present example includes a pump (38) and a microbe removal air filter (40) that filters microbes from an incoming air stream.

A pressure switch or sensor (42) is in fluid communication with each flush line (30) for sensing excessive pressure in the flush line. Any excessive pressure or lack of flow sensed may be indicative of a partial or complete blockage (e.g., by bodily tissue or dried bodily fluids) in an endoscope (200) channel to which the relevant flush line (30) is connected. The isolation of each flush line (30) relative to the other flush lines (30) allows the particular blocked channel to be easily identified and isolated, depending upon which sensor (42) senses excessive pressure or lack of flow.

Basin (14a) is in fluid communication with a water source (50), such as a utility or tap water connection including hot and cold inlets, and a mixing valve (52) flowing into a break tank (56). A microbe removal filter (54), such as a 0.2 μm or smaller absolute pore size filter, decontaminates the incoming water, which is delivered into break tank (56) through the air gap to prevent backflow. A sensor (59) monitors liquid levels within basin (14a). An optional water heater (53) can be provided if an appropriate source of hot water is not available. The condition of filter (54) can be monitored by directly monitoring the flow rate of water therethrough or indirectly by monitoring the basin fill time using a float switch or the like. When the flow rate drops below a select threshold, this indicates a partially clogged filter element that requires replacement.

A basin drain (62) drains liquid from basin (14a) through an enlarged helical tube (64) into which elongated portions of endoscope (200) can be inserted. Drain (62) is in fluid communication with a recirculation pump (70) and a drain pump (72). Recirculation pump (70) recirculates liquid from basin drain (62) to a spray nozzle assembly (60), which sprays the liquid into basin (14a) and onto endoscope (200). A coarse screen (71) and a fine screen (73) filter out particles in the recirculating fluid. Drain pump (72) pumps liquid from basin drain (62) to a utility drain (74). A level sensor (76) monitors the flow of liquid from pump (72) to utility drain (74). Pumps (70, 72) can be simultaneously operated such that liquid is sprayed into basin (14a) while basin (14a) is being drained, to encourage the flow of residue out of basin (14a) and off of endoscope (200). Of course, a single pump and a valve assembly could replace dual pumps (70, 72).

An inline heater (80), with temperature sensors (82), upstream of recirculation pump (70), heats the liquid to optimum temperatures for cleaning and/or disinfection. A pressure switch or sensor (84) measures pressure downstream of circulation pump (70). In some variations, a flow sensor is used instead of pressure sensor (84), to measure fluid flow downstream of circulation pump (70). Detergent solution (86) is metered into the flow downstream of circulation pump (70) via a metering pump (88). A float switch (90) indicates the level of detergent (86) available. Disinfectant (92) is metered into the flow upstream of circulation pump (70) via a metering pump (94). To more accurately meter disinfectant (92), a dispensing pump (94) fills a metering pre-chamber (96) under control of a fluid level switch (98) and control system (20). By way of example only, disinfection solution (92) may comprise CIDEX© Activated Glutaraldehyde Solution by Advanced Sterilization Products of Irvine, Calif. By way of further example only, disinfection solution (92) may comprise ortho-phthalaldehyde (OPA). By way of further example only, disinfection solution (92) may comprise peracetic acid (PAA).

Some endoscopes (200) include a flexible outer housing or sheath surrounding the individual tubular members and the like that form the interior channels and other parts of endoscope (200). This housing defines a closed interior space, which is isolated from patient tissues and fluids during medical procedures. It may be important that the sheath be maintained intact, without cuts or other holes that would allow contamination of the interior space beneath the sheath. Therefore, reprocessing system (2) of the present example includes means for testing the integrity of such a sheath. In particular, an air pump (e.g., pump (38) or another pump (110)) pressurizes the interior space defined by the sheath of endoscope (200) through a conduit (112) and a valve (S5). In the present example, a HEPA or other microbe-removing filter (113) removes microbes from the pressurizing air. A pressure regulator (114) prevents accidental over pressurization of the sheath. Upon full pressurization, valve (S5) is closed and a pressure sensor (116) looks for a drop in pressure in conduit (112), which would indicate the escape of air through the sheath of endoscope (200). A valve (S6) selectively vents conduit (112) and the sheath of endoscope (200) through an optional filter (118) when the testing procedure is complete. An air buffer (120) smoothes out pulsation of pressure from air pump (110).

In the present example, each station (10, 12) also contains a drip basin (130) and spill sensor (132) to alert the operator to potential leaks.

An alcohol supply (134), controlled by a valve (S3), can supply alcohol to channel pumps (32) after rinsing steps, to assist in removing water from channels (210, 212, 213, 214, 217, 218) of endoscope (200).

Flow rates in supply lines (30) can be monitored via channel pumps (32) and pressure sensors (42). If one of pressure sensors (42) detects too high a pressure, the associated pump (32) is deactivated. The flow rate of pump (32) and its activated duration time provide a reasonable indication of the flow rate in an associated line (30). These flow rates are monitored during the process to check for blockages in any of the channels of endoscope (200). Alternatively, the decay in the pressure from the time pump (32) cycles off can also be used to estimate the flow rate, with faster decay rates being associated with higher flow rates.

A more accurate measurement of flow rate in an individual channel may be desirable to detect more subtle blockages. To that end, a metering tube (136) having a plurality of level indicating sensors (138) fluidly connects to the inputs of channel pumps (32). In some versions, a reference connection is provided at a low point in metering tube (136) and a plurality of sensors (138) are arranged vertically above the reference connection. By passing a current from the reference point through the fluid to sensors (138), it can be determined which sensors (138) are immersed and therefore determine the level within metering tube (136). In addition or in the alternative, any other suitable components and techniques may be used to sense fluid levels. By shutting valve (S1) and opening a vent valve (S7), channel pumps (32) draw exclusively from metering tube (136). The amount of fluid being drawn can be very accurately determined based upon sensors (138). By running each channel pump (32) in isolation, the flow therethrough can be accurately determined based upon the time and the volume of fluid emptied from metering tube (136).

In addition to the input and output devices described above, all of the electrical and electromechanical devices shown are operatively connected to and controlled by control system (20). Specifically, and without limitation, switches and sensors (42, 59, 76, 84, 90, 98, 114, 116, 132 136) provide input (I) to microcontroller (28), which controls the cleaning and/or disinfection cycles and other machine operations in accordance therewith. For example, microcontroller (28) includes outputs (0) that are operatively connected to pumps (32, 38, 70, 72, 88, 94, 100, 110), valves (S1, S2, S3, S5, S6, S7), and heater (80) to control these devices for effective cleaning and/or disinfection cycles and other operations.

Figure 3:
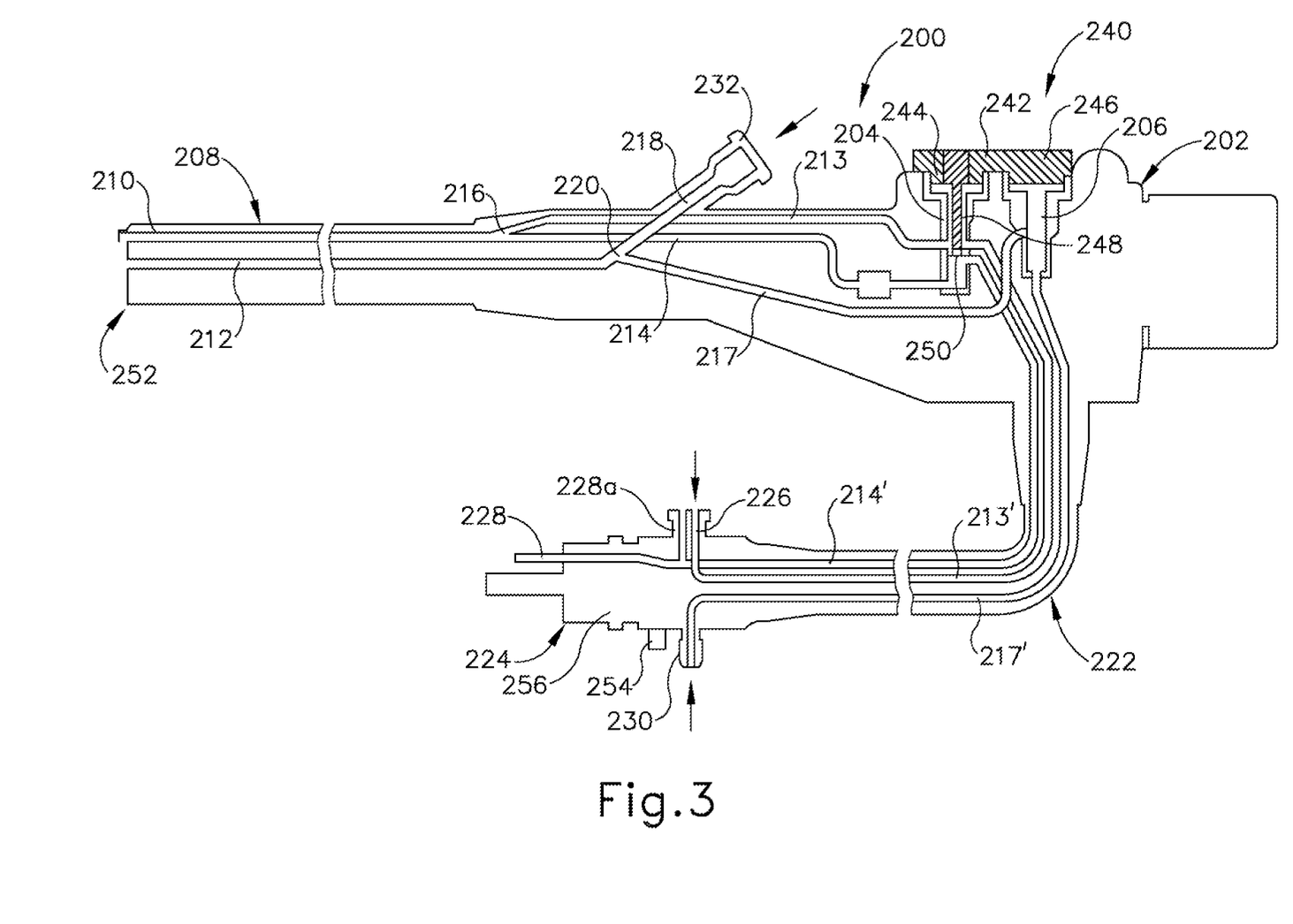
FIG. 3 depicts a cross-sectional side view of proximal and distal portions of an endoscope that may be decontaminated using the reprocessing system of FIG. 1.

As shown in FIG. 3, endoscope (200) has a head part (202). Head part (202) includes openings (204, 206) formed therein. During normal use of endoscope (200), an air/water valve (not shown) and a suction valve (not shown) are arranged in openings (204, 206). A flexible insertion tube (208) is attached to head part (202). A combined air/water channel (210) and a combined suction/biopsy channel (212) are accommodated in insertion tube (208). A separate air channel (213) and water channel (214) are also arranged in head part (202) and merge into air/water channel (210) at the location of a joining point (216). It will be appreciated that the term "joining point" as used herein refers to an intersecting junction rather than being limited to a geometrical point and, the terms may be used interchangeably. Furthermore, a separate suction channel (217) and biopsy channel (218) are accommodated in head part (202) and merge into suction/biopsy channel (212) at the location of a joining point (220).

In head part (202), air channel (213) and water channel (214) open into opening (204) for the air/water valve (not shown). Suction channel (217) opens into opening (206) for the suction valve (not shown). Furthermore, a flexible feed hose (222) connects to head part (202) and accommodates channels (213', 214', 217'), which are connected to air channel (213), water channel (214), and suction channel (217) via respective openings (204, 206). In practice, feed hose (222) may also be referred to as the light-conductor casing. The mutually connecting air channels (213, 213') will collectively be referred to below as air channel (213).

The mutually connecting water channels (214, 214') will collectively be referred to below as water channel (214). The mutually connecting suction channels (217, 217') will collectively be referred to below as suction channel (217). A connection (226) for air channel (213), connections (228, 228a) for water channel (214), and a connection (230) for suction channel (217) are arranged on the end section (224) (also referred to as the light conductor connector) of flexible hose (222). When the connection (226) is in use, connection (228a) is closed off. A connection (232) for biopsy channel (218) is arranged on head part (202).

A channel separator (240) is shown inserted into openings (204, 206). Channel separator (240) comprises a body (242) and plug members (244, 246), which occlude respective openings (204, 206). A coaxial insert (248) on plug member (244) extends inwardly of opening (204) and terminates in an annular flange (250), which occludes a portion of opening (204) to separate channel (213) from channel (214). By connecting lines (30) to openings (226, 228, 228a, 230, 232), liquid for cleaning and disinfection can be flowed through endoscope channels (213, 214, 217, 218) and out of a distal tip (252) of endoscope (200) via channels (210, 212). Channel separator (240) ensures that such liquid flows all the way through endoscope (200) without leaking out of openings (204, 206); and isolates channels (213, 214) from each other so that each channel (213, 214) has its own independent flow path. One of skill in the art will appreciate that various endoscopes having differing arrangements of channels and openings may require modifications to channel separator (240) to accommodate such differences while occluding ports in head (202) and keeping channels separated from each other so that each channel can be flushed independently of the other channels. Otherwise, a blockage in one channel might merely redirect flow to a connected unblocked channel.

A leakage port (254) on end section (224) leads into an interior portion (256) of endoscope (200) and is used to check for the physical integrity thereof, namely to ensure that no leakage has formed between any of the channels and the interior (256) or from the exterior to the interior (256).

II. Exemplary Medical Device Reprocessing Method

In an exemplary use of reprocessing system (2), an operator may start by actuating a foot pedal (not shown) to open basin lid (16a). Each lid (16a, 16b) may have its own foot pedal. In some versions, once pressure is removed from the foot pedal, the motion of lid (16a, 16b) stops. With lid (16a) open, the operator inserts insertion tube (208) of endoscope (200) into helical circulation tube (64). End section (224) and head section (202) of endoscope (200) are situated within basin (14a), with feed hose (222) coiled within basin (14a) with as wide a diameter as possible. Next, flush lines (30) are attached to respective endoscope openings (226, 228, 228a, 230, 232). Air line (112) is also connected to connector (254). In some versions, flush lines (30) are color coded, and guide located on station (10) provides a reference for the color-coded connections.

Depending on the customer-selectable configuration, control system (20) may prompt the operator to enter a user code, patient ID, endoscope code, and/or specialist code. This information may be entered manually (e.g., through touch screen (22)), automatically (e.g., by using an attached barcode wand), or in any other suitable fashion. With the information entered (if required), the operator may then close lid (16a). In some versions, closing lid (16a) requires the operator to press a hardware button and a touch-screen (22) button simultaneously to provide a fail-safe mechanism for preventing the operator's hands from being caught or pinched by the closing basin lid (16a). If either the hardware button or software button is released while lid (16a) is in the process of closing, the motion of lid (16a) stops.

Once lid (16a) is closed, the operator presses a button on touch-screen (22) to begin the washing/disinfection process. At the start of the washing/disinfection process, air pump (38) is activated and pressure within the body of endoscope (200) is monitored. When pressure reaches a predetermined level (e.g., 250 mbar), pump (38) is deactivated, and the pressure is allowed to stabilize for a certain stabilization period (e.g., 6 seconds). If pressure has not reached a certain pressure (e.g., 250 mbar) in a certain time period (e.g., 45 seconds), the program is stopped and the operator is notified of a leak. If pressure drops below a threshold (e.g., less than 100 mbar) during the stabilization period, the program is stopped and the operator is notified of the condition. Once the pressure has stabilized, the pressure drop is monitored over the course of a certain duration (e.g., 60 seconds). If pressure drop is faster than a predetermined rate (e.g., more than 10 mbar within 60 seconds), the program is stopped and the operator is notified of the condition. If the pressure drop is slower than a predetermined rate (e.g., less than 10 mbar in 60 seconds), reprocessing system (2) continues with the next step. A slight positive pressure is held within the body of endoscope (200) during the rest of the process to prevent fluids from leaking in.

A second leak test checks the adequacy of connection to the various ports (226, 228, 228a, 230, 232) and the proper placement of channel separator (240). A quantity of water is admitted to basin (14a) so as to submerge the distal end of endoscope (200) in helical tube (64). Valve (S1) is closed and valve (S7) opened; and pumps (32) are run in reverse to draw a vacuum and to ultimately draw liquid into endoscope channels (210, 212). Pressure sensors (42) are monitored to make sure that the pressure in any one channel (210, 212) does not drop and/or raise by more than a predetermined amount in a given time frame. If it does, it likely indicates that one of the connections was not made correctly and air is leaking into channel (210, 212). In any event, in the presence of an unacceptable pressure drop, control system (20) will cancel the cycle and indicate a likely faulty connection, preferably with an indication of which channel (210, 212) failed.

In the event that the leak tests are passed, reprocessing system (2) continues with a pre-rinse cycle. The purpose of this step is to flush water through channels (210, 212, 213, 214, 217, 218) to remove waste material prior to washing and disinfecting endoscope (200). To initiate the pre-rinse cycle, basin (14a) is filled with filtered water and the water level is detected by pressure sensor (59) below basin (14a). The water is pumped via pumps (32) through the interior of channels (210, 212, 213, 214, 217, 218), directly to drain (74). This water is not recirculated around the exterior surfaces of endoscope 200 during this stage. As the water is being pumped through channels (210, 212, 213, 214, 217, 218), drain pump (72) is activated to ensure that basin (14a) is also emptied. Drain pump (72) will be turned off when drain switch (76) detects that the drain process is complete. During the draining process, sterile air is blown via air pump (38) through all endoscope channels (210, 212, 213, 214, 217, 218) simultaneously, to minimize potential carryover.

Once the pre-rinse cycle is complete, reprocessing system (2) continues with a wash cycle. To begin the wash cycle, basin (14a) is filled with warm water (e.g., approximately 35° C.). Water temperature is controlled by controlling the mix of heated and unheated water. The water level is detected by pressure sensor (59). Reprocessing system (2)

then adds enzymatic detergent to the water circulating in reprocessing system (2) by means of peristaltic metering pump (88). The volume is controlled by controlling the delivery time, pump speed, and inner diameter of the tubing of pump (88). Detergent solution (86) is actively pumped throughout the internal endoscope channels (210, 212, 213, 214, 217, 218) and over the outer surface of endoscope (200) for a predetermined time period (e.g., from one to five minutes, or more particularly about three minutes), by channel pumps (32) and external circulation pump (70). Inline heater (80) keeps the temperature at a predetermined temperature (e.g., approximately about 35° C.).

After detergent solution (86) has been circulating for a certain period of time (e.g., a couple of minutes), the flow rate through channels (210, 212, 213, 214, 217, 218) is measured. If the flow rate through any channel (210, 212, 213, 214, 217, 218) is less than a predetermined rate for that channel (210, 212, 213, 214, 217, 218), the channel (210, 212, 213, 214, 217, 218) is identified as blocked, the program is stopped, and the operator is notified of the condition. Peristaltic pumps (32) are run at their predetermined flow rates and cycle off in the presence of unacceptably high pressure readings at the associated pressure sensor (42). If a channel (210, 212, 213, 214, 217, 218) is blocked, the predetermined flow rate will trigger pressure sensor (42), indicating the inability to adequately pass this flow rate. As pumps (32) are peristaltic in the present example, their operating flow rate combined with the percentage of time they are cycled off due to pressure will provide the actual flow rate. The flow rate can also be estimated based upon the decay of the pressure from the time pump (32) cycles off.

At the end of the wash cycle, drain pump (72) is activated to remove detergent solution (86) from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover.

After the wash cycle is complete, reprocessing system (2) begins a rinse cycle. To initiate this rinse cycle, basin (14a) is again filled with warm water (e.g., at approximately 35° C.). Water temperature is controlled by the mix of heated and unheated water. The water level is detected by pressure sensor (59). The rinse water is circulated within channels (210, 212, 213, 214, 217, 218) of endoscope (200) via channel pumps (32); and over the exterior of endoscope (200) via circulation pump (70) and sprinkler arm (60) for a certain period of time (e.g., one minute). As rinse water is pumped through channels (210, 212, 213, 214, 217, 218), the flow rate through channels (210, 212, 213, 214, 217, 218) is measured and if it falls below the predetermined rate for any given channel (210, 212, 213, 214, 217, 218), that channel (210, 212, 213, 214, 217, 218) is identified as blocked, the program is stopped, and the operator is notified of the condition.

At the end of the rinse cycle, drain pump (72) is activated to remove the rinse water from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover. In some versions, the above-described rinsing and draining cycles are repeated at least once again, to ensure maximum rinsing of detergent solution (86) from the surfaces of endoscope (200) and basin (14a).

After reprocessing system (2) has completed the desired number of rinsing and drying cycles, reprocessing system (2) proceeds to a disinfection cycle. To initiate the disinfection cycle, basin (14a) is filled with very warm water (e.g., at approximately 53° C.). Water temperature is controlled by controlling the mix of heated and unheated water. The water level is detected by pressure sensor (59). During the filling process, channel pumps (32) are off in order to ensure that the disinfection solution (92) in basin (14a) is at the in-use concentration prior to circulating through channels (210, 212, 213, 214, 217, 218) of endoscope (200).

Next, a measured volume of disinfection solution (92) is drawn from disinfectant metering pre-chamber (96) and delivered into the water in basin (14a) via metering pump (100). The volume of disinfection solution (92) is controlled by the positioning of fill level switch (98) relative to the bottom of metering pre-chamber (96). Metering pre-chamber (96) is filled until fill level switch (98) detects liquid. Disinfection solution (92) is drawn from metering pre-chamber (96) until the level of disinfection solution (92) in metering pre-chamber (96) is just below the tip of metering pre-chamber (96). After the necessary volume is dispensed, metering pre-chamber (96) is refilled from the bottle of disinfection solution (92). Disinfection solution (92) is not added until basin (14a) is filled, so that in case of a water supply problem, concentrated disinfectant is not left on endoscope (200) with no water to rinse it. While disinfection solution (92) is being added, channel pumps (32) are off in order to ensure that disinfection solution (92) in basin (14a) is at the desired in-use concentration prior to circulating through channels (210, 212, 213, 214, 217, 218) of endoscope (200).

The in-use disinfectant solution (92) is actively pumped throughout internal channels (210, 212, 213, 214, 217, 218) by pumps (32) and over the outer surface of endoscope (200) by circulation pump (70). This may be done for any suitable duration (e.g., at least 5 minutes). The temperature of the disinfection solution (92) may be controlled by in-line heater (80) to stay at a consistent temperature (e.g., about 52.5° C.). During the disinfection process, flow through each channel (210, 212, 213, 214, 217, 218) of endoscope (200) is verified by timing the delivering a measured quantity of solution through channel (210, 212, 213, 214, 217, 218). Valve (S1) is closed, and valve (S7) opened, and in turn each channel pump (32) delivers a predetermined volume to its associated channel (210, 212, 213, 214, 217, 218) from metering tube (136). This volume and the time it takes to deliver the volume, provides a very accurate flow rate through the channel (210, 212, 213, 214, 217, 218). Anomalies in the flow rate from what is expected for a channel (210, 212, 213, 214, 217, 218) of that diameter and length are flagged by control system (20) and the process stopped. As in-use disinfection solution (92) is pumped through channels (210, 212, 213, 214, 217, 218), the flow rate through channels (210, 212, 213, 214, 217, 218) is also measured as described above.

At the end of the disinfection cycle, drain pump (72) is activated to remove disinfection solution (92) solution from basin (14a) and channels (210, 212, 213, 214, 217, 218). During the draining process, sterile air is blown through all channels (210, 212, 213, 214, 217, 218) of endoscope (200) simultaneously to minimize potential carryover. As will be described in greater detail below, in some versions, the used disinfection solution (92) is tested to determine whether the concentration level is within an acceptable range or if the used disinfection solution (92) has been diluted to a point where the used disinfection solution (92) is below a certain concentration threshold. If the used disinfection solution (92) has acceptable concentration level, the used disinfection solution (92) may be used again in subsequent disinfection cycles. If the used disinfection solution (92) has a concentration below the threshold, the used disinfection solution (92) may be disposed of (e.g., via drain (74)).

After disinfection solution (92) has been drained from basin (14a), reprocessing system (2) begins a final rinse cycle. To initiate this cycle, basin (14a) is filled with sterile warm water (e.g., at approximately 45° C.) that has been passed through a filter (e.g., a 0.2 µm filter). The rinse water is circulated within channels (210, 212, 213, 214, 217, 218) by pumps (32); and over the exterior of endoscope (200) via circulation pump (70) and sprinkler arm 60) for a suitable duration (e.g., 1 minute). As rinse water is pumped through channels (210, 212, 213, 214, 217, 218), the flow rate through channels (210, 212, 213, 214, 217, 218) is measured as described above. Drain pump (72) is activated to remove the rinse water from basin (14a) and channels (210, 212, 213, 214, 217, 218). During the draining process, sterile air is blown through all channels (210, 212, 213, 214, 217, 218) of endoscope (200) simultaneously to minimize potential carryover. In some versions, the above-described rinsing and draining cycles are repeated at least two more times, to ensure maximum rinsing of disinfection solution (92) residuals from the surfaces of endoscope (200) and basin (14a).

After the final rinse cycle is complete, reprocessing system (2) begins a final leak test. In particular, reprocessing system (2) pressurizes the body of endoscope (200) and measures the leak rate as described above. If the final leak test is successful, reprocessing system (2) indicates the successful completion of the cycles via touch-screen (22). From the time of program completion to the time at which lid (16a) is opened, pressure within the body of endoscope (200) is normalized to atmospheric pressure by opening vent valve (S5) at a predetermined rate (e.g., valve (S5) opened for 10 seconds every minute).

Depending on customer-selected configuration, reprocessing system (2) may prevent lid (16a) from being opened until a valid user identification code is entered. Information about the completed program, including the user ID, endoscope ID, specialist ID, and patient ID are stored along with the sensor data obtained throughout the program. If a printer is connected to reprocessing system (2), and if requested by the operator, a record of the disinfection program will be printed. Once a valid user identification code has been entered, lid (16a) may be opened (e.g., using the foot pedal as described above). Endoscope (200) is then disconnected from flush lines (30) and removed from basin (14a). Lid (16a) can then be closed using both the hardware and software buttons as described above.

III. Exemplary Disinfectant Concentration Measuring Subsystem

As noted above, some versions of reprocessing system (2) may provide just a single use of a certain volume of disinfection solution (92), such that the used volume of disinfection solution (92) is disposed of after a single use of the volume of disinfection solution (92) upon completion of the disinfection cycle. As also noted above, some other versions of reprocessing system (2) may check the concentration level of a used volume of disinfection solution (92) and either re-use the used disinfection solution (92) (i.e., if the concentration level is still acceptable) or dispose of the used disinfection solution (92) (i.e., if the concentration level is no longer acceptable). Merely illustrative examples of versions of reprocessing system (2) that provide monitoring and re-use of disinfection solution (92) are disclosed in U.S. Pat. No. 8,246,909, entitled "Automated Endoscope Reprocessor Germicide Concentration Monitoring System and Method," issued Aug. 21, 2012, the disclosure of which is incorporated by reference herein; and in U.S. patent application Ser. No. 15/157,800, entitled "Apparatus and Method for Reprocessing a Medical Device," filed on even date herewith and issued as U.S. Pat. No. 10,201,269 on Feb. 12, 2019, the disclosure of which is incorporated by reference herein.

Figure 4:
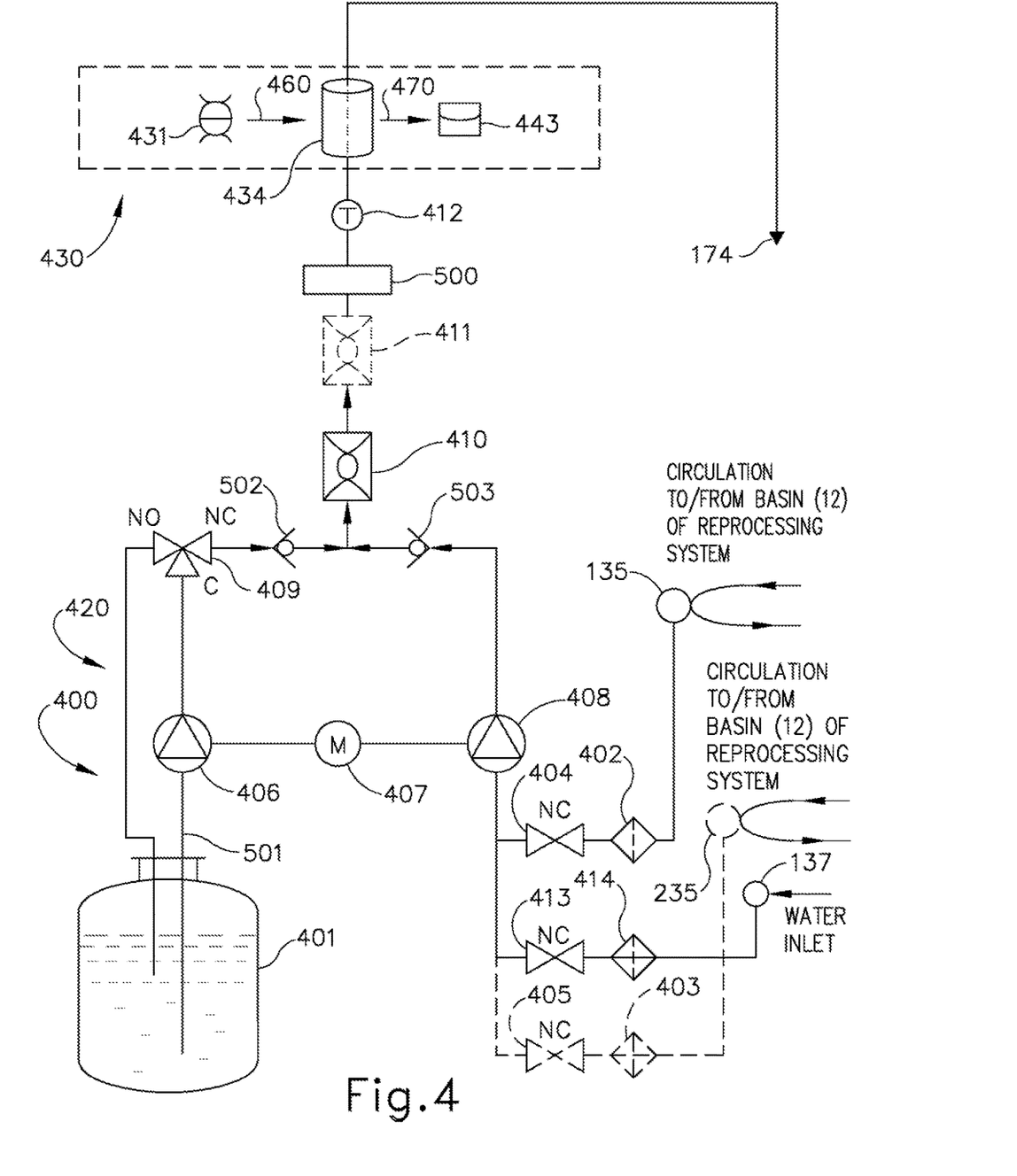
FIG. 4 is a diagrammatic illustration of a disinfectant concentration measuring subsystem that may be incorporated into the reprocessing system of FIG. 1.
Figure 5:
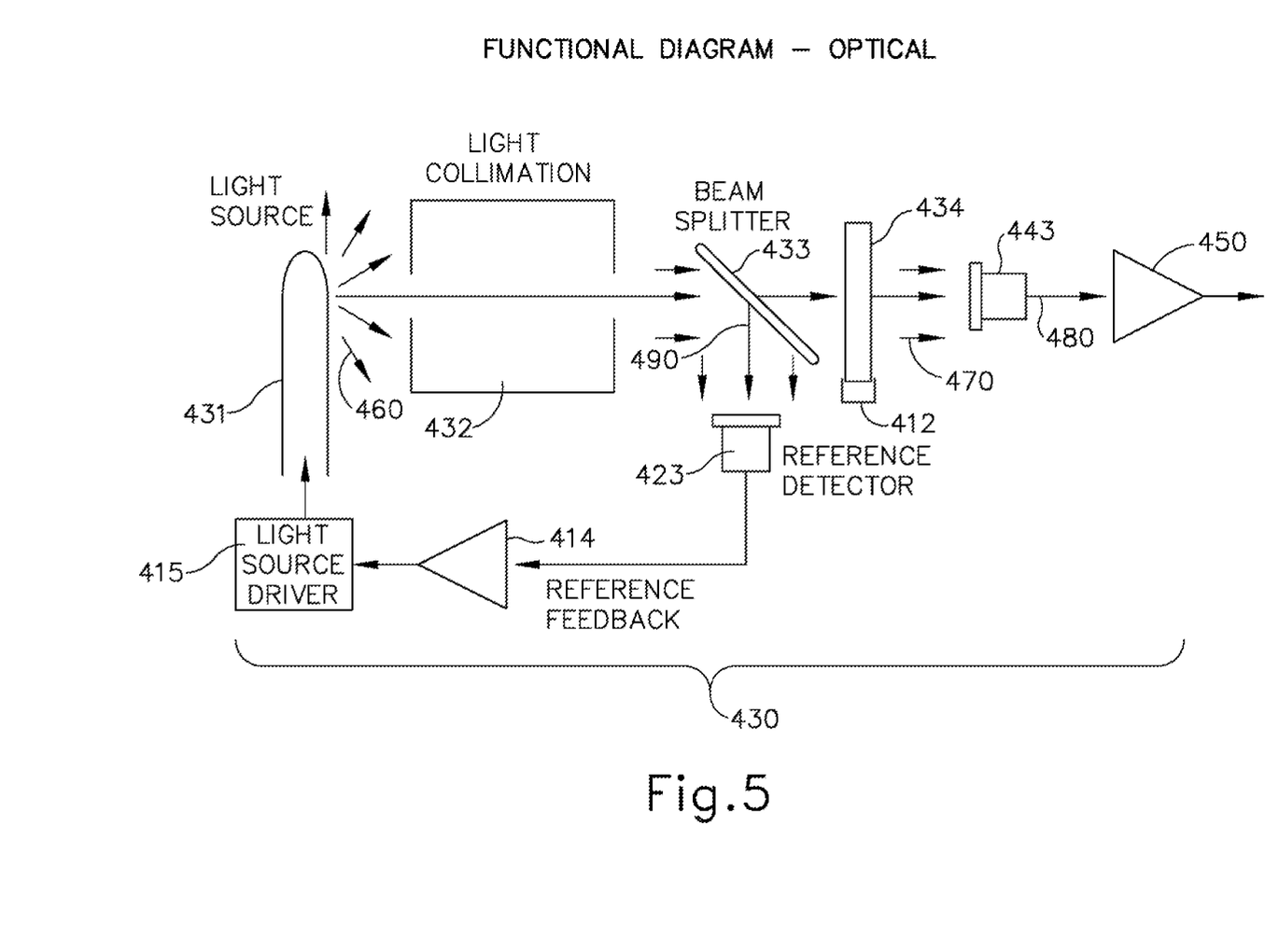
FIG. 5 is a diagrammatic illustration of an optical portion of the disinfectant concentration measuring subsystem of FIG. 4.

FIGS. 4-5 show diagrammatic illustrations of an exemplary disinfectant concentration measuring subsystem (400), hereinafter, "subsystem (400)." Subsystem (400) measures disinfectant concentration of disinfection solution (92) that is used, and often re-circulated and re-used, in reprocessing system (2). Although subsystem (400) of this example may be used to measure disinfectant concentration of disinfection solution (92) in reprocessing system (2) comprising either one station (10) or optionally, two stations (10, 12), it is contemplated herein that subsystem (400) may be readily adapted by one skilled in the art to sample disinfection solution (92) from a reprocessing system comprising three or more stations. Subsystem (400) may be combined with reprocessing system (2) in a number of ways. For example, subsystem (400) may be fully integrated into reprocessing system (2). In a further example, subsystem (400) may be provided as a separate stand-alone unit that is placed in fluid communication with reprocessing system (2) (e.g., by coupling subsystem (400) with reprocessing system (2) via a fluid conduit, etc.). It should also be understood that subsystem (400) may be incorporated into reprocessing system (2) in accordance with the teachings of U.S. Pat. No. 8,246,909 and/or the teachings of U.S. patent application Ser. No. 15/157,800, entitled "Apparatus and Method for Reprocessing a Medical Device," filed on even date herewith and issued as U.S. Pat. No. 10,201,269 on Feb. 12, 2019. Various other suitable ways in which subsystem (400) may be combined with reprocessing system (2) will be apparent to those of ordinary skill in the art in view of the teachings herein.

FIG. 4 shows a functional diagram of exemplary fluidics system (420) of subsystem (400). Fluidics system (420) may be configured for batch processing or continuous processing of disinfection solution (92). Fluidics system (420) is connected to a first outlet (135) of reprocessing system (2). First outlet (135) provides circulation with first station (10). Fluidics system (420) is also connected to a second outlet (235) of reprocessing system (2). Second outlet (235) provides circulation with second station (12). It should be understood that, since second station (12) is merely optional, second outlet (235) is also merely optional.

First outlet (135) is also in fluid communication with first filter (402). First filter (402) is in fluid communication with first valve (404), which is normally in a closed state. If present, second outlet (235) is likewise in fluid communication with second filter (403). Second filter (403) is in fluid communication with second valve (405), which is normally in a closed state. Normally closed first valve (404) is opened when disinfection solution (92) is to be sampled from first station (10), and alternatively, normally closed second valve (405) is opened when disinfection solution (92) is to be sampled from second station (12). In any case, when first and/or second valves (404, 405) are closed, and motor ((407) discussed below) stopped, subsystem (400) is in holding mode, and disinfection solution (92) is free to circulate to and from reprocessing system (2). In order for continuous sampling of disinfection solution (92) to occur, either first valve (404) or optional second valve (405) remains in an open state.

Fluidics system (420) of the present example is also in fluid communication with reservoir (401) that is configured to contain reagent solution. Reservoir (401) is in fluid communication with first pump (406), whereas aforementioned first valve (404) and optional second valve (405) are in fluid communication with second pump (408). In some versions such as the one shown in FIG. 4, first pump (406) and second pump (408) are simultaneously driven by dual-head stepper motor (407). Utilizing dual-head stepper motor (407) allows for precise and accurate control of volumetric flow of reagent solution and disinfection solution (92) through respective pumps (406, 408). For example, disinfection solution (92) and reagent solution may be simultaneously pumped at volumetric flow rate ratio of about 1:1. Alternatively, some other kind of motor and/or pumping arrangement may be used to pump at volumetric flow rate ratio of about 1:1 or any other desired volumetric flow rate ratio. Moreover, motor and/or pumping arrangements may be configured to change the volumetric flow rate ratio in real time, such as for example, by driving two pumps via two different motors to respectively pump the disinfection solution (92) and the reagent solution.

In the example shown in FIG. 4, first pump (406) is in fluid communication with selector valve (409), which is in fluid communication with first mixing chamber (410). Selector valve (409) controls flow of reagent solution either back to reservoir (401) or to first mixing chamber (410). In the present example, when selector valve (409) is in the normally open state, reagent solution flows from reservoir (401), through first pump (406) and back into reservoir (401), which may allow for reagent supply line (501) to be purged and de-gassed without wasting reagent solution. Various suitable devices and methods that may be used to purge and/or de-gas reagent supply line (501) will be apparent to those of ordinary skill in the art in view of the teachings herein. It should also be understood that such purging and de-gassing features are merely optional. Some versions may simply omit such purging and de-gassing features.

When disinfection solution (92) is to be measured for disinfectant concentration, the normally open portion of selector valve (409) closes and the normally closed portion of selector valve (409) opens to allow reagent solution to flow from reservoir (401), through first pump (406), through first check valve (502) and into first mixing chamber (410). First check valve (502) prevents flow back of fluid from first mixing chamber (410) back through selector valve (409) and ultimately back into reservoir (401) where the fluid may contaminate the reagent. In order for continuous sampling of disinfection solution (92) to occur, selector valve (409) may remain in this position to continuously deliver reagent solution to first mixing chamber (410).

In fluidics system (420) of the present example, second pump (408) is also in fluid communication with first mixing chamber (410). Thus, when either first valve (404) or alternatively, optional second valve (405) is in an open state, disinfection solution (92) is pumped through second check valve (503) and into first mixture chamber (410). Second check valve (503) prevents flow back of fluid from first mixing chamber (410) back into second pump (408). As noted above, in the present example shown in FIG. 4, first pump (406) and second pump (408) are simultaneously driven by dual-head stepper motor (407), which allows for precise and accurate control of volumetric flow of reagent solution and disinfection solution (92) respectively through pumps (406, 408). Thus, volumes of reagent solution and disinfection solution (92) delivered into first mixing chamber (410) may be precisely controlled and consequently, may be mixed in any desired ratio within first mixing chamber (410) to create sample solution. In some versions, reagent solution and disinfection solution (92) may be mixed in a volume to volume ratio of about 1:1 to create sample solution.

As shown in FIG. 4, fluidics system (420) is also connected to water inlet (137). Water inlet (137) is in fluid communication with third filter (414). Third filter (414) is in fluid communication with third valve (413), which is normally in a closed position. Normally closed third valve (413) is opened when a baseline concentration of reagent product is to be determined. When third valve (413) is open, a volume of water (instead of a volume of disinfection solution (92)) is mixed in the first mixing chamber (410) with a volume of reagent solution to create a blank solution. In some versions, reagent solution and water may be mixed in a volume to volume ratio of about 1:1 to create the blank solution. Absorbance of the blank solution is measured, as described below, and utilized by controller (450) to calculate absorbance of reaction product(s) of interest.

As shown in FIG. 4, first mixing chamber (410) may optionally be in fluid communication with second mixing chamber (411). It is contemplated herein that more than two mixing chambers (410, 411) may be utilized. By way of example only, mixing chambers (410, 411) may each comprise a static mixer with a plurality of mixing elements. Various suitable forms that mixing chambers (410, 411) may take will be apparent to those of ordinary skill in the art in view of the teachings herein. One skilled in the art may chose the number of mixing chambers to include in subsystem (400) based upon a number of factors including, but not limited to, sample mixing time needed to generate reaction product having concentration in sample solution (or blank solution) that is measurable utilizing concentration analysis assembly (430) of subsystem (400). In any case, one or more of mixing chamber(s) (410, 411) are in fluid communication with de-gassing module (500). De-gassing module (500) is operable to remove air bubbles from the liquid solution passing through mixing chamber(s) (410, 411). Degassing module (500) is in fluid communication with sample chamber (434). It should be understood that degassing module (500) is merely optional. In some versions, degassing module (500) is omitted entirely.

In the present example, sample chamber (434) is a cuvette having transparent (or otherwise optically tramsissive) sides. In some versions, cuvette (434) is formed from optical quartz and has straight sides for minimal interference in measuring light passing therethrough.

Depending upon the chemical reaction that is desired when the reagent solution is mixed with the disinfection solution (92), the temperature of the resulting sample solution may impact the absorbance measurement of the reaction product in the sample solution. Thus, in some versions, such as the one shown in FIG. 4, subsystem (400) includes temperature sensor (412), which is positioned such that it may measure the temperature of sample solution as the sample solution passes from mixing chamber (410, 411) into sample chamber (434). Temperature sensor (412) measures the temperature of sample solution to allow for temperature corrections by a controller (not shown) when determining disinfectant concentration in disinfection solution (92). It should be understood that temperature sensor (412) is merely optional. In some versions, temperature sensor (412) is omitted entirely.

Concentration analysis assembly (430) of subsystem (400) is generally shown to comprise light emitting diode (431) and a photodiode sensor (443). Light emitting diode (431) is configured to emit light of first known intensity (460) and wavelength and to direct light through sample chamber (434). Sensor (443) measures a portion of light that passes through cuvette (434) and which has second intensity (470).

FIG. 5 shows another exemplary configuration that may be used to form concentration analysis assembly (430) of subsystem (400). Concentration analysis assembly (430) of FIG. 5 comprises light source (431) that emits light having known first intensity (460) and wavelength. Light source (431) emits and directs light through collimator (432), beam splitter (433), cuvette (434) containing sample solution, and sensor (443). Cuvette (434) may be formed of optical quartz and has straight sides for minimal interference in measuring light passing there through. A portion of light (490) is reflected to reference detector (423) to regulate power supply (415) to light source (431) and ensure consistent output therefrom. The portion of light that passes through cuvette (434) has second intensity (470). The portion of light having second intensity (470) then travels through sensor (443) having inlet filter, through which light having a wavelength of from about 570 nm plus or minus 120 nm may pass. Light output (480) from sensor (443) is sent to controller (450).

In some versions, light source (431) emits light having a wavelength in a range of from about 500 nanometers ("nm") to about 600 nm. More particularly, light source (431) may emit light having a wavelength of about 570 nm. In some versions, light source (431) may emit light of a first known intensity (460) of from about 70 millicandela (mcd) to about 120 mcd. As subsystem (400) ages, the first known intensity (460) may be adjusted by one skilled in the art in order to compensate for any aging effects on the light intensity (e.g., increased cloudiness of the cuvette window of subsystem (400), etc.).

The difference between known first light intensity (460) and second light intensity (470) is indicative of reaction product concentration in sample solution or blank solution. Controller (450) is configured to determine the concentration of reaction product in sample solution based upon sensed light data from sensor (443) in accordance with the Beer-Lambert law. Based upon the concentration of reaction product in sample solution, controller (450) is configured to determine the concentration of disinfectant in disinfection solution (92).

As can be seen in FIG. 5, a thermistor (412) is configured to measure temperature of cuvette (434). Controller (450) may be configured to adjust the determination of disinfectant concentration due to any thermal impact on light measurements, as detected by thermistor (412).

In some versions, control system (20) is further configured to issue an alert signal when a concentration of disinfectant in disinfection solution (92) is below a predetermined value that is indicative of disinfection solution (92) that no longer contains an effective concentration of disinfectant. When this alert signal is sent, it indicates to a user of reprocessing system (2) that disinfection solution (92) should be replaced to ensure that disinfection solution (92) is sufficiently concentrated to provide for effective sterilization or disinfection of the next endoscope(s) to be cleaned. By way of example only, the alert signal may comprise one or more of the following: an audible sound, a warning message through visual display (22), a text message sent to a smartphone, a pop-up message sent to a computing device (e.g., a desktop computer, laptop computer, tablet, smartphone, etc.), and/or combinations thereof. The alert signal may also interface with a hospital inventory management system and automatically request delivery of more disinfectant solution (92) to reprocessing system (2). The alert signal may even trigger the automatic ordering of more disinfectant solution (92) from a manufacturer. Other suitable forms that an alert signal may take, and other kinds of actions that may be triggered in response to an alert signal, will be apparent to those of ordinary skill in the art in view of the teachings herein.

In the present example, for OPA-containing disinfection solution (92) to be effective in a given sterilization or disinfection cycle, the minimum effective concentration of OPA in disinfection solution (92) is about 0.3% by weight of disinfection solution (92). For PAA-containing disinfection solution (92) to be effective in any given sterilization or disinfection cycle, and by way of example only, the minimum effective amount of PAA in disinfection solution (92) is from about 0.10% to about 0.30%, or from about 0.15% to 0.25% by weight of disinfection solution (92). More particularly, the minimum effective concentration of PAA in disinfection solution (92) may be about 0.15% by weight of disinfection solution (92).

Determination of the concentration of reaction product in the sample solution, may be performed in response to manual user input or on an automatic basis. For example, a user may push a button (e.g., a button labeled "test disinfectant concentration," etc.) to provide a manual input initiating determination of disinfectant concentration. Such manual input may be provided on an ad hoc basis or on a periodic basis. If performed on an automatic basis, determination of disinfectant concentration may be initiated on bases selected from: on the basis of time (e.g., every Monday at 9:00 AM), on the basis of number of uses (e.g., after every ten endoscope sterilizations), on the basis of a total cycle time (e.g., after every ten hours of sterilization cycles), and/or on some other basis, including combinations thereof.

As shown in FIG. 4, if the sample solution is no longer of use, the sample solution is outputted from concentration analysis assembly (430) of subsystem (400) via fluid output (174). Fluid output (174) may be coupled with one or more drains, for example, utility drain (74) of reprocessing system (2).

IV. Exemplary Method for Measuring Disinfectant Concentration

Figure 6:
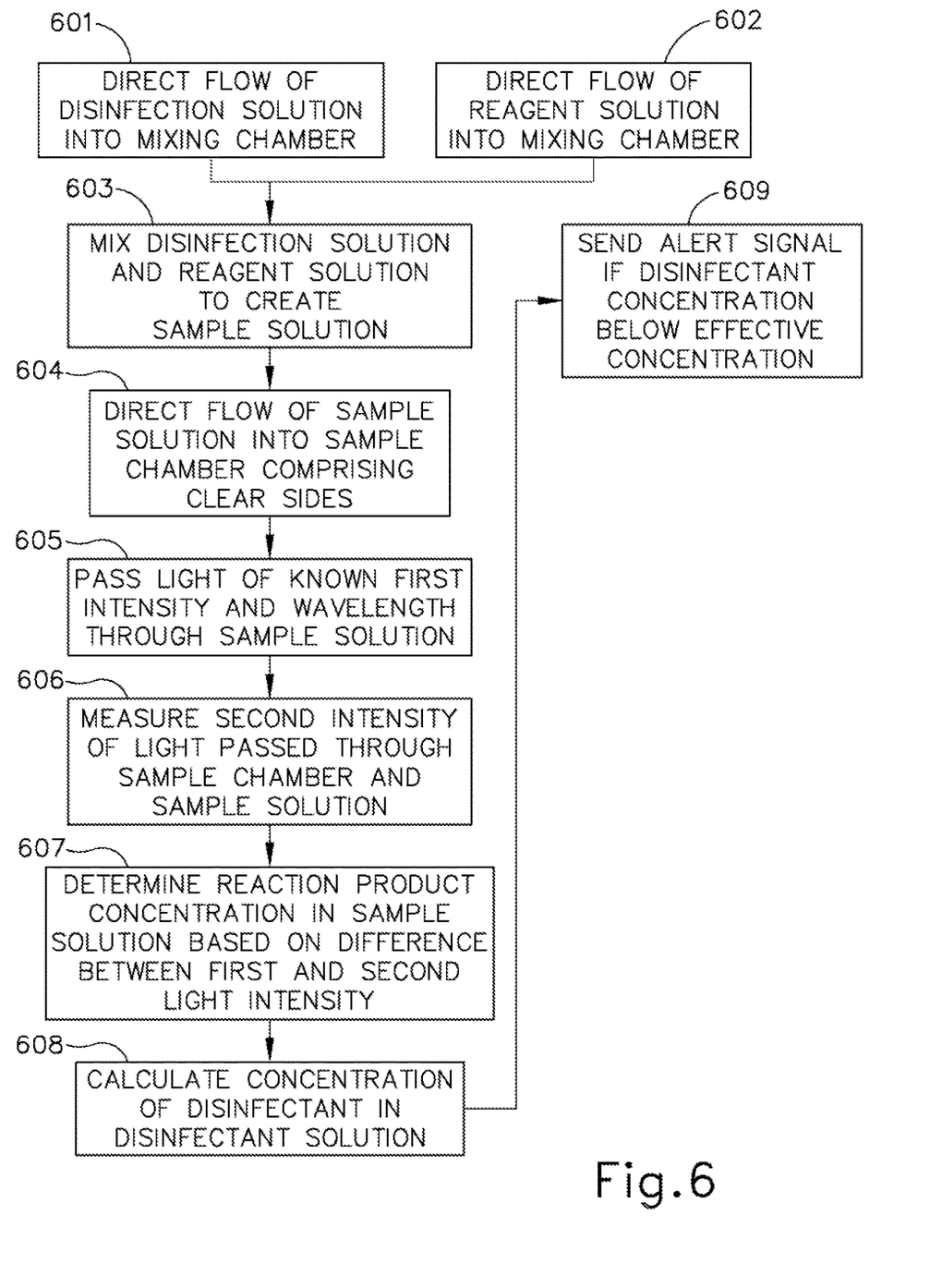
FIG. 6 depicts a flow chart of a method that may be carried out using the disinfectant concentration measuring subsystem of FIG. 4 to measure a concentration of a disinfectant in a disinfection solution.

Subsystem (400) may measure disinfectant concentration in disinfection solution (92) in reprocessing system (2). As shown in FIG. 6, measuring of disinfectant concentration begins with step (601), whereby flow of disinfection solution (92) is directed into first mixing chamber (410). Step (601) is performed simultaneously with step (602). In step (602), flow of reagent solution is directed into first mixing chamber (410). Thereafter, in step (603), disinfection solution (92) and reagent solution are mixed to create sample solution. Step (604) follows step (603). In step (604), flow of sample solution is directed into sample chamber (434) comprising clear sides. Step (605) follows step (604). In step (605), light having known first intensity and wavelength is passed through sample chamber and sample solution in sample chamber. In some versions, step (605) is performed simultaneously with step (606). In some other versions, steps (605, 606) are performed separately or overlappingly in a sequence. In step (606), second intensity of light passed through sample chamber and sample solution in sample chamber is measured. Step (607) follows step (606). In step (607), reaction product concentration in sample solution is determined based upon a difference between known first light intensity and second light intensity. Step (608) follows step (607). In step (608), disinfectant concentration in disinfection solution (92) is determined based upon reaction product concentration. Step (609) follows step (608). In step (609), alert signal is sent if disinfectant concentration in disinfection solution is below an effective concentration.

V. Exemplary Reagent Solutions

When disinfection solution (92) is mixed with reagent solution, a sample solution is made. Exemplary reagent solutions comprise one or more substances that undergo reaction(s) with disinfectant solution (92) to form reaction product(s) in the sample solution. As described in detail above, a concentration of reaction product(s) in the sample solution is measured and used to determine disinfectant concentration in disinfection solution (92).

Reagent solutions as described herein may overcome issues associated with non-reagent based techniques for measuring concentration of aldehyde-containing disinfectants by passing a light through a sample thereof. For example, the present reagent solutions may react with disinfectant in a solution such that the absorbance of aldehydes and/or reaction products in the sample solution do not interfere with measuring the disinfectant concentration. Moreover, reagent solutions as described herein may be successfully utilized to measure a wider range of disinfectant concentrations in sample solutions (i.e., from very low to very high disinfectant concentrations in sample solutions). Moreover, the use of the presently described reagent solutions may allow for increased accuracy in determining disinfectant concentration in a sample solution, thus allowing for precise determination of disinfectant concentration around a point of interest, such as a minimum effective concentration of disinfectant in the sample solution.

To measure OPA concentration in disinfection solution (92), an exemplary reagent solution comprising components having the following functions may be utilized:
(a) reactant that will react with OPA to form hydroxide;
(b) acid to react with the hydroxide;
(c) pH indicator/absorbance species;
(d) solvent; and optionally
(e) pH indicator/absorbance species solubility enhancer.

Exemplary reactants that will react with OPA to form hydroxide are sulfites selected from sodium sulfite, sodium bisulfite and combinations thereof.

Exemplary acids to react with the hydroxide are selected from hydrochloric acid, sulfuric acid, nitric acid, phosphoric acid, organic carboxylic acids and combinations thereof. Exemplary organic carboxylic acids are selected from acetic acid, formic acid, citric acid, oxalic acid, propionic acid and combinations thereof.

Exemplary pH indicators/absorbance species are selected from phenolphthalein, O-cresolphthalein, p-naphtholbenzene, ethyl-bis(2,4-dimethylphenyl)acetate and thymolphthalein.

An exemplary solvent is water.

Exemplary pH indicator/absorbance species solubility enhancers are selected from ethanol, isopropanol, n-propanol, n-butanol, isobutanol, propylene glycol, ethylene glycol, dimethyl sulfoxide, N,N-dimethylformamide and combinations thereof.

An exemplary reagent solution for measuring OPA concentration in disinfection solution (92) may be made by mixing together by weight percentage of the total weight of the reagent solution the following raw materials:
(a) from about to about 1% to about 5%, or more particularly about 3%, sodium sulfite;
(b) from about 0.1% to about 0.2%, or more particularly about 0.175%, of 37% hydrochloric acid;
(c) from about to about 0.002% to about 0.008%, or more particularly about 0.004%, phenolphthalein;
(d) from about to about 10% to about 20%, or more particularly 15.7%, isopropanol; and
(e) wherein the balance is water, or more particularly 81.1% water.

Upon mixing raw materials together, a reaction occurs between hydrochloric acid and sodium sulfite to produce sodium bisulfite and sodium chloride. Thus, ready-to-use reagent solution for measuring OPA concentration in disinfection solution (92) comprises:
(a) from about 1% to about 4.8%, or more particularly about 2.78%, sodium sulfite;
(b) from about 0.1% to about 0.3%, or more particularly about 0.185%, sodium bisulfite;
(c) from about 0.06% to about 0.12%, or more particularly about 0.104%, sodium chloride;
(d) from about 0.002% to about 0.008%, or more particularly about 0.004%, phenolphthalein;
(e) from about 10% to about 20%, or more particularly 15.7% isopropanol; and
(f) wherein the balance is water, or more particularly 81.2% water.

Without wishing to be bound by theory, it is believed that when ready-to-use reagent solution for measuring OPA concentration is mixed with disinfection solution (92), OPA present in disinfection solution (92) reacts with excess sodium sulfite to quantitatively generate hydroxide, which is neutralized by a controlled amount of acid (including acid from reagent solution and dihydrogen phosphate and benzotriazole from OPA solution). If OPA is present in disinfection solution (92) at a concentration of greater than about 0.3% by weight of the disinfection solution (92), then excess hydroxide will be generated in the sample solution, resulting in an increase in pH and phenolphthalein absorbance that are interpreted by controller (450) as "pass." If, on the other hand, OPA present in disinfection solution (92) at below about 0.3% by weight percent of the disinfection solution (92), then excess acid will be present in the sample solution, resulting in decrease in pH and phenolphthalein absorbance that is interpreted by controller (92) to read as "fail."

To measure PAA concentration in disinfection solution (92), an exemplary reagent solution comprising soluble iodide(s) may be utilized. Exemplary soluble iodide(s) are selected from potassium iodide, sodium iodide, calcium iodide, magnesium iodide and combinations thereof. Upon mixing the reagent solution with PAA-containing disinfection solution (92) to form a sample solution, PAA reacts with the soluble iodide in about a 1:1 volume ratio to form iodine in the sample solution. Controller (450) is configured to utilize absorbance of iodine in the sample solution to determine concentration of PAA in disinfection solution (92).

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A medical instrument processor comprising: (a) an enclosure for holding a medical instrument; (b) a liquid distribution system configured to deliver a disinfection solution to a medical instrument within the enclosure, the liquid distribution system comprising a liquid outlet; (c) a disinfectant concentration measuring subsystem comprising: (i) a first mixing chamber in fluid communication with the liquid outlet, (ii) a reservoir configured to contain a reagent solution, wherein the reservoir is in fluid communication with the first mixing chamber, (iii) a pump that is configured to simultaneously pump the disinfection solution and the reagent solution into the first mixing chamber, and (iv) a concentration analysis assembly that is operable to determine a concentration of disinfectant in a sample solution that is output from the first mixing chamber.

Example 2

The medical instrument processor of claim 1, wherein the concentration analysis assembly comprises: (A) a sample chamber comprising optically transmissive sides, (B) a light source configured to pass light of a known first intensity and wavelength through the sample chamber and the sample solution in the sample chamber, and (C) a sensor configured to measure a second intensity of the light passing through the sample chamber and the sample solution in the sample chamber.

Example 3

The medical instrument processor of claim 2, wherein the light source comprises a light emitting diode.

Example 4

The medical instrument processor of claim 2, wherein the sensor comprises a photodiode.

Example 5

The medical instrument processor of claim 2, wherein the disinfectant concentration measuring subsystem further comprises a control system that is configured to: (i) determine a reaction product concentration in the sample solution based upon a difference between the known first intensity and the second intensity of the light, and (ii) determine a concentration of disinfectant in the disinfection solution based upon the reaction product concentration in the sample solution.

Example 6

The medical instrument processor of claim 5, wherein the control system is further configured to issue an alert signal when the concentration of disinfectant in the disinfection solution is below a predetermined value.

Example 7

The medical instrument processor of claim 5, wherein the disinfectant comprises ortho-phthalaldehyde and the reaction product comprises sodium hydroxide.

Example 8

The medical instrument processor of claim 5, wherein the disinfectant comprises peracetic acid and the reaction product comprises iodine.

Example 9

The medical instrument processor of claim 5, wherein the disinfectant concentration measuring subsystem further comprises a temperature sensor configured to measure a temperature of the sample solution.

Example 10

The medical instrument processor of claim 9, wherein the control system is further configured to adjust the disinfectant concentration in the disinfection solution based upon the temperature of the sample solution.

Example 11

The medical instrument processor of claim 1, wherein the pump comprises a dual-head stepper motor.

Example 12

The medical instrument processor of claim 1, wherein the pump is configured to simultaneously pump the disinfection solution and the reagent solution at volumetric flow rate ratio of about 1:1.

Example 13

The medical instrument processor of claim 1, wherein the disinfectant is selected from ortho-phthalaldehyde and peracetic acid.

Example 14

The medical instrument processor of claim 1, wherein the mixing chamber comprises a static mixer.

Example 15

The medical instrument processor of claim 1, wherein the disinfectant concentration measuring subsystem further comprises a second mixing chamber in fluid communication with the first mixing chamber.

Example 16

A method for measuring a concentration of a disinfectant in a disinfection solution of a medical instrument processor, the method comprising: (a) directing a flow of the disinfection solution into a first mixing chamber; (b) directing a flow of a reagent solution into the first mixing chamber; (c) mixing the disinfection solution and the reagent solution in the first mixing chamber to create a sample solution; (d)

directing the sample solution into a sample chamber comprising clear sides; (e) passing light having a known first intensity and wavelength through the clear sides of the sample chamber and the sample solution in the sample chamber; (f) measuring a second intensity of the light transmitted through the sample chamber and the sample solution in the sample chamber; (g) determining a reaction product concentration in the sample solution based upon a difference between the known first intensity and the second intensity of the light; and (h) determining the disinfectant concentration in the disinfection solution based upon the reaction product concentration.

Example 17

The method of claim 16, wherein the disinfectant is selected from ortho-phthalaldehyde and peracetic acid.

Example 18

The method of claim 16, wherein the disinfection solution and the reagent solution are mixed in a volume to volume ratio of about 1:1 to create the sample solution.

Example 19

The method of claim 13, further comprising issuing an alert signal when the disinfectant concentration in the disinfection solution is below a predetermined value.

Example 20

A reagent solution for measuring OPA concentration in disinfection solution (92) is made by mixing together by weight percentage of the total weight of the reagent solution the following raw materials: (a) from about 1% to about 5% sodium sulfite; (b) from about 0.1% to about 0.2 of 37% hydrochloric acid; (c) from about 0.002% to about 0.008% phenolphthalein; (d) from about 10% to about 20% isopropanol; and (e) a balance of water.

Example 21

A reagent solution for measuring OPA concentration in disinfection solution (92) is made by mixing together by weight percentage of the total weight of the reagent solution the following raw materials: (a) about 3% sodium sulfite; (b) about 0.175%, of 37% hydrochloric acid; (c) about 0.004% phenolphthalein; (d) about 15.7% isopropanal; and (d) about 81.1% water.

Example 22

A ready-to-use reagent solution comprises by weight percentage of the total weight of the ready-to-use reagent solution: (a) from about 1% to about 4.8% sodium sulfite; (b) from about 0.1% to about 0.3% sodium bisulfite; (c) from about 0.06% to about 0.12% sodium chloride; (d) from about 0.002% to about 0.008% phenolphthalein; (e) from about 10% to about 20% isopropanol; and (f) a balance of water.

Example 23

A ready-to-use reagent consisting essentially of: a) from about 1% to about 4.8% sodium sulfite; (b) from about 0.1% to about 0.3% sodium bisulfate; (c) from about 0.06% to about 0.12% sodium chloride; (d) from about 0.002% to about 0.008% phenolphthalein; (e) from about 10% to about 20% isopropanol; and (f) a balance of water.

Example 24

A ready-to-use reagent consisting essentially of: a) about 2.78% sodium sulfite; (b) about 0.185% sodium bisulfite; (c) about 0.104% sodium chloride; (d) about 0.004% phenolphthalein; (e) about 15.7% isopropanol; and (f) about 81.2% water.

VII. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for measuring a concentration of a disinfectant in a disinfection solution of a medical instrument processor, the method comprising:
    (a) directing a flow of the disinfection solution into a first mixing chamber;
    (b) directing a flow of a reagent solution into the first mixing chamber;
    (c) mixing the disinfection solution and the reagent solution in the first mixing chamber to create a sample solution;
    (d) directing the sample solution into a sample chamber comprising clear sides;
    (e) passing light having a known first intensity and wavelength through the clear sides of the sample chamber and the sample solution in the sample chamber;
    (f) measuring a second intensity of the light transmitted through the sample chamber and the sample solution in the sample chamber;
    (g) determining a reaction product concentration in the sample solution based upon a difference between the known first intensity and the second intensity of the light; and
    (h) determining the disinfectant concentration in the disinfection solution based upon the reaction product concentration;
    wherein the reaction product is sodium hydroxide.

2. The method of claim 1, wherein the disinfectant comprises ortho-phthalaldehyde.

3. The method of claim 1, wherein the disinfection solution and the reagent solution are mixed in a volume to volume ratio of about 1:1 to create the sample solution.

4. The method of claim 1, further comprising issuing an alert signal when the disinfectant concentration in the disinfection solution is below a predetermined value.

5. The method of claim 1, further comprising:
  (a) determining that the disinfectant concentration in the disinfection solution is below a predetermined value; and
  (b) outputting the disinfectant solution from the medical instrument processor.

6. The method of claim 1, further comprising:
  (a) determining that the disinfectant concentration in the disinfection solution is not below a predetermined value; and
  (b) recirculating the disinfectant solution in the medical instrument processor.

7. The method of claim 1, comprising simultaneously directing the flow of the disinfection solution and the reagent solution into the first mixing chamber.

8. The method of claim 1, further comprising:
  (a) directing the disinfection solution and the reagent solution into a second mixing chamber; and
  (b) mixing the disinfection solution and the reagent solution in the second mixing chamber to generate the sample solution.

9. The method of claim 8, comprising:
  (a) mixing the disinfection solution and the reagent solution in the first mixing chamber using a static mixer; and
  (b) mixing the disinfection solution and the reagent solution in the second mixing chamber using a static mixer to generate the sample solution.

10. The method of claim 1, further comprising directing the sample solution into a de-gassing module, prior to directing the sample solution into the sample chamber.

11. The method of claim 1, further comprising measuring the temperature of the sample solution as it passes from the first mixing chamber into the sample chamber.

12. The method of claim 11, further comprising making temperature corrections when determining the disinfectant concentration in the disinfection solution based upon the reaction product concentration.

13. The method of claim 8, further comprising directing the sample solution into a de-gassing module prior to directing the sample solution into the sample chamber.

14. The method of claim 8, further comprising measuring the temperature of the sample solution as it passes from the second mixing chamber into the sample chamber.

15. The method of claim 14, further comprising making temperature corrections when determining the disinfectant concentration in the disinfection solution based upon the reaction product concentration.

16. A method for measuring a concentration of a disinfectant in a disinfection solution of a medical instrument processor, the method comprising:
  (a) mixing the disinfection solution and a reagent solution in one or more mixing chambers to generate a sample solution;
  (b) directing the sample solution into a sample chamber;
  (c) passing light having a first intensity and wavelength through the sample chamber and the sample solution in the sample chamber;
  (d) measuring a second intensity of the light transmitted through the sample chamber and the sample solution in the sample chamber;
  (e) calculating a concentration of sodium hydroxide in the sample solution based upon a difference between the first intensity of the light and the second intensity of the light; and
  (f) determining the disinfectant concentration in the disinfection solution based upon the concentration of sodium hydroxide in the sample solution.

17. The method of claim 16, further comprising:
  (a) determining that the disinfectant concentration in the disinfection solution is below a predetermined value; and
  (b) outputting the disinfectant solution from the medical instrument processor.

18. The method of claim 16, further comprising:
  (a) determining that the disinfectant concentration in the disinfection solution is not below a predetermined value; and
  (b) recirculating the disinfectant solution in the medical instrument processor.

19. A method for determining a concentration of ortho-phthalaldehyde in a disinfection solution of a medical instrument processor, the method comprising:
  (a) mixing the disinfection solution and a reagent solution in one or more mixing chambers to generate a sample solution;
  (b) directing the sample solution into a sample chamber;
  (c) passing light having a first intensity of from about 70 millicandela to about 120 millicandela and a wavelength of from about 500 nanometers to about 600 nanometers through the sample chamber and the sample solution in the sample chamber;
  (d) measuring a second intensity of the light transmitted through the sample chamber and the sample solution in the sample chamber;
  (e) calculating a concentration of sodium hydroxide in the sample solution based upon a difference between the first intensity of the light and the second intensity of the light; and
  (f) determining the concentration of ortho-phthalaldehyde in the disinfection solution based upon the calculated concentration of sodium hydroxide.

20. The method of claim 19, further comprising either:
  (a) determining that the disinfectant concentration in the disinfection solution is below a predetermined value and outputting the disinfectant solution from the medical instrument processor; or
  (b) determining that the disinfectant concentration in the disinfection solution is not below a predetermined value and recirculating the disinfectant solution in the medical instrument processor.

* * * * *